US 6,740,308 B2
United States Patent
Rabinowitz et al.

Date of Patent: May 25, 2004

(54) DELIVERY OF ANTIHISTAMINES THROUGH AN INHALATION ROUTE

(75) Inventors: Joshua D. Rabinowitz, Mountain View, CA (US); Alejandro C. Zaffaroni, Atherton, CA (US)

(73) Assignee: Alexza Molecular Delivery Corporation, Palo Alto, CA (US)

(*) Notice: Subject to any disclaimer, the term of this patent is extended or adjusted under 35 U.S.C. 154(b) by 0 days.

(21) Appl. No.: 10/153,831

(22) Filed: May 21, 2002

(65) Prior Publication Data

US 2003/0015189 A1 Jan. 23, 2003

Related U.S. Application Data

(60) Provisional application No. 60/294,203, filed on May 24, 2001, and provisional application No. 60/317,479, filed on Sep. 5, 2001.

(51) Int. Cl.[7] .............................. A61K 9/12; A61K 9/14
(52) U.S. Cl. .............................. 424/45; 424/46; 424/43; 128/200.14; 128/200.24; 128/203.12; 125/203.17
(58) Field of Search ................ 424/45, 46; 128/200.24, 128/203.12, 200.14; 125/203.17

(56) References Cited

U.S. PATENT DOCUMENTS

| | | | |
|---|---|---|---|
| 3,219,533 A | 11/1965 | Mullins | |
| 4,183,912 A | 1/1980 | Rosenthale | |
| RE30,285 E | 5/1980 | Babington | |
| 4,232,002 A | 11/1980 | Nogrady | |
| 5,099,861 A | 3/1992 | Clearman et al. | |
| 5,388,574 A | 2/1995 | Ingebrethsen | |
| 5,455,043 A | 10/1995 | Fischel-Ghodsian | |
| 5,457,100 A | 10/1995 | Daniel | |
| 5,544,646 A | 8/1996 | Lloyd et al. | |
| 5,694,919 A | 12/1997 | Rubsamen et al. | |
| 5,735,263 A | 4/1998 | Rubsamen et al. | |
| 5,758,637 A | 6/1998 | Ivri et al. | |
| 5,915,378 A | 6/1999 | Lloyd et al. | |
| 5,934,272 A | 8/1999 | Lloyd et al. | |
| 5,957,124 A | 9/1999 | Lloyd et al. | |
| 5,960,792 A | 10/1999 | Lloyd et al. | |
| 6,041,777 A | * 3/2000 | Faithfull et al. | ........ 128/200.24 |
| 6,095,134 A | 8/2000 | Sievers et al. | |
| 6,095,153 A | 8/2000 | Kessler et al. | |
| 6,102,036 A | 8/2000 | Slutsky et al. | |
| 6,133,327 A | 10/2000 | Kimura et al. | |
| 6,514,482 B1 | * 2/2003 | Bartus et al. | ................. 424/45 |
| 6,591,839 B2 | 7/2003 | Meyer et al. | |
| 2002/0058009 A1 | 5/2002 | Bartus et al. | |
| 2002/0061281 A1 | 5/2002 | Osbkken et al. | |
| 2003/0032638 A1 | 2/2003 | Kim et al. | |

FOREIGN PATENT DOCUMENTS

| | | |
|---|---|---|
| EP | 0 358 114 | 3/1990 |
| WO | WO 92/05781 | 4/1992 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 97/27804 | 8/1997 |
| WO | WO 98/22170 | 5/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/17568 | 3/2001 |

OTHER PUBLICATIONS

Bennett, R.L. et al. (1981). "Patient–Controlled Analgesia: A New Concept of Postoperative Pain Relief," *Annual Surg.* 195(6):700–705.

Carroll, M.E. et al. (1990), "Cocaine–base smoking in rhesus monkeys: reinforcing and physiological effects," *Psychopharmacology* (Berl). 102:443–450.

Clark, A. and Byron, P. (1986). "Dependence of Pulmonary Absorption Kinetics on Aerosol Particle Size," *Z. Erkrank.* 166:13–24.

Darquenne, C. et al. (1997). "Aerosol Dispersion in Human Lung: Comparison Between Numerical Simulations and Experiments for Bolus Tests," *American Physiological Society.* 966–974.

(List continued on next page.)

*Primary Examiner*—Michael G. Hartley
*Assistant Examiner*—Mina Haghighatian
(74) *Attorney, Agent, or Firm*—Elaine C. Stracker

(57) ABSTRACT

The present invention relates to the delivery of antihistamines through an inhalation route. Specifically, it relates to aerosols containing antihistamines that are used in inhalation therapy. In a composition aspect of the present invention, the aerosol comprises particles comprising at least 5 percent by weight of an antihistamine. In a method aspect of the present invention, an antihistamine is delivered to a mammal through an inhalation route. The method comprises: a) heating a composition, wherein the composition comprises at least 5 percent by weight of an antihistamine, to form a vapor; and, b) allowing the vapor to cool, thereby forming a condensation aerosol comprising particles, which is inhaled by the mammal. In a kit aspect of the present invention, a kit for delivering an antihistamine through an inhalation route to a mammal is provided which comprises: a) a composition comprising at least 5 percent by weight of an antihistamine; and, b) a device that forms an antihistamine containing aerosol from the composition, for inhalation by the mammal.

16 Claims, 1 Drawing Sheet

OTHER PUBLICATIONS

Davies, C.N. et al. (May 1972). "Breathing of Half–Micron Aerosols," *Journal of Applied Physiology.* 32(5):591–600.

Dershwitz, M., M.D., et al. (Sep. 2000)."Pharmacokinetics and Pharmacodynamics of Inhaled versus Intravenous Morphine in Healthy Volunteers," *Anesthesiology.* 93(3): 619–628.

Finlay, W.H. (2001). "The Mechanics of Inhaled Pharmaceutical Aerosols", Academic Press: San Diego Formula 2.39. pp.3–14 (Table of Contents). pp. v–viii.

Gonda,I. (1991). "Particle Deposition in the Human Respiratory Tract," Chapter 176, *The Lung:Scientific Foundations.* Crystal R.G. and West, J.B. (eds.), Raven Publishers, New York. pp. 2289–2294.

Hatsukami D, et al. (May 1990) "A method for delivery of precise doses of smoked cocaine–base to humans." *Pharmacology Biochemistry & Behavior.* 36(1):1–7.

Heyder, J. et al. (1986). "Deposition of Particles in the Human Respiratory Tract in the Size Range 0.005–15 $\mu$m," *J. Aerosol Sci.* 17(5):811–822.

Huizer, H., "Analytical studies on illicit heron. V. Efficacy of volatilization during heroin smoking." *Pharmaceutisch Weekblad Scientific Edition* (1987). 9(4):203–211.

Hurt, R.D., MD and Robertson, C.R., PhD, (Oct. 1998). "Prying Open the Door to the Tobacco Industry's Secrets About Nicotine: The Minnesota Tobacco Trial," *JAMA* 280(13):1173–1181.

Lichtman, A.H. et al. (1996). "Inhalation Exposure to Volatilized Opioids Produces Antinociception in Mice," Journal of Pharmacology and Experimental Therapeutics. 279(1):69–76.

Martin, B.R. and Lue, L.P. (May/Jun. 1989). "Pyrolysis and Volatilization of Cocaine," *Journal of Analytical Toxicology* 13:158–162.

Mattox, A.J. and Carroll, M.E., (1996). "Smoked heroin self–administration in rhesus monkeys," *Psychopharmacology,* 125:195–201.

Meng, Y. et al. "Inhalation Studies With Drugs of Abuse," *NIDA Research Monograph,* (1997) 173:201–224.

Meng, Y., et al. (1999). "Pharmacological effects of methamphetamine and other stimulants via inhalation exposure," *Drug and Alcohol Dependence.* 53:111–120.

Pankow, J.F. et al. (1997). "Conversion of Nicotine in Tobacco Smoke to Its Volatile and Available Free–Base Form Through the Action of Gaseous Ammonia," *Envron. Sci. Technol.* 31:2428–2433.

Pankow, J. (Mar. 2000). ACS Conference–San Francisco–Mar. 26, 2000. Chemistry of Tobacco Smoke. pp. 1–8.

Seeman, J. et al. (1999). "The Form of Nicotine in Tobacco. Thermal Transfer of Nicotine and Nicotine Acid Salts to Nicotine in the Gas Phase," *J. Agric. Food Chem.* 47(12):5133–5145.

Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271–1280.

Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," *Clinical Pharmacology & Therapeutics* 62(6):596–609.

Wood, R.W. et al. (1996). "Generation of Stable Test Atmospheres of Cocaine Base and Its Pyrolyzate, Methylecgonidine, and Demonstration of Their Biological Activity." *Pharmacology Biochemistry & Behavior.* 55(2):237–248.

Office Action mailed Aug. 13, 2003 for US application 10/153,313 filed May 21, 2002 "Delivery of Benzodiazepines Through an Inhalation Route".

* cited by examiner

DELIVERY OF ANTIHISTAMINES THROUGH AN INHALATION ROUTE

This application claims priority to U.S. provisional application Ser. No. 60/294,203 entitled "Thermal Vapor Delivery of Drugs," filed May 24, 2001, Rabinowitz and Zaffaroni, the entire disclosure of which is hereby incorporated by reference. This application further claims priority to U.S. provisional application Ser. No. 60/317,479 entitled "Aerosol Drug Delivery," filed Sep. 5, 2001, Rabinowitz and Zaffaroni, the entire disclosure of which is hereby incorporated by reference.

FIELD OF THE INVENTION

The present invention relates to the delivery of antihistamines through an inhalation route. Specifically, it relates to aerosols containing antihistamines that are used in inhalation therapy.

BACKGROUND OF THE INVENTION

There are a number of antihistamine containing compositions currently marketed for the treatment of allergy symptoms. The compositions contain at least one active ingredient that provides for observed therapeutic effects. Among the active ingredients in such compositions are azatadine, brompheniramine, carbinoxamine, chlorpheniramine, clemastine, cyproheptadine, loratadine, pyrilamine, hydroxyzine, and promethazine.

It is desirable to provide a new route of administration for antihistamines that rapidly produces peak plasma concentrations of the compound. The provision of such a route is an object of the present invention.

SUMMARY OF THE INVENTION

The present invention relates to the delivery of antihistamines through an inhalation route. Specifically, it relates to aerosols containing antihistamines that are used in inhalation therapy.

In a composition aspect of the present invention, the aerosol comprises particles comprising at least 5 percent by weight of an antihistamine. Preferably, the particles comprise at least 10 percent by weight of an antihistamine. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of an antihistamine.

Typically, the antihistamine is not one of the following antihistamines: dexmedetomidine, diphenhydramine, doxylamine, loratidine, and promethazine.

Typically, the aerosol has a mass of at least 0.10 $\mu$g. Preferably, the aerosol has a mass of at least 100 $\mu$g. More preferably, the aerosol has a mass of at least 200 $\mu$g.

Typically, the aerosol particles comprise less than 10 percent by weight of antihistamine degradation products. Preferably, the particles comprise less than 5 percent by weight of antihistamine degradation products. More preferably, the particles comprise less than 2.5, 1, 0.5, 0.1 or 0.03 percent by weight of antihistamine degradation products.

Typically, the aerosol particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.85. More preferably, the geometric standard deviation is less than 2.7.

Typically, the aerosol is formed by heating a composition containing an antihistamine to form a vapor and subsequently allowing the vapor to condense into an aerosol.

In another composition aspect of the present invention, the aerosol comprises particles comprising at least 5 percent by weight of azatadine, brompheniramine, carbinoxamine, chlorpheniramine, clemastine, cyproheptadine, loratadine, pyrilamine, hydroxyzine, or promethazine. Preferably, the particles comprise at least 10 percent by weight of azatadine, brompheniramine, carbinoxamine, chlorpheniramine, clemastine, cyproheptadine, loratadine, pyrilamine, hydroxyzine, or promethazine. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of azatadine, brompheniramine, carbinoxamine, chlorpheniramine, clemastine, cyproheptadine, loratadine, pyrilamine, hydroxyzine, or promethazine.

Typically, the aerosol has a mass of at least 0.10 $\mu$g. Preferably, the aerosol has a mass of at least 100 $\mu$g. More preferably, the aerosol has a mass of at least 200 $\mu$g.

Typically, the aerosol particles comprise less than 10 percent by weight of azatadine, brompheniramine, carbinoxamine, chlorpheniramine, clemastine, cyproheptadine, loratadine, pyrilamine, hydroxyzine, or promethazine degradation products. Preferably, the particles comprise less than 5 percent by weight of azatadine, brompheniramine, carbinoxamine, chlorpheniramine, clemastine, cyproheptadine, loratadine, pyrilamine, hydroxyzine, or promethazine degradation products. More preferably, the particles comprise less than 2.5, 1, 0.5, 0.1 or 0.03 percent by weight of azatadine, brompheniramine, carbinoxamine, chlorpheniramine, clemastine, cyproheptadine, loratadine, pyrilamine, hydroxyzine, or promethazine degradation products.

Typically, the aerosol particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the aerosol comprises azatadine, the aerosol has an inhalable aerosol drug mass density of between 0.2 mg/L and 2.5 mg/L. Preferably, the aerosol has an inhalable aerosol drug mass density of between 0.35 mg/L and 2 mg/L. More preferably, the aerosol has an inhalable aerosol drug mass density of between 0.5 mg/L and 1.5 mg/L.

Typically, where the aerosol comprises clemastine, the aerosol has an inhalable aerosol drug mass density of between 0.25 mg/L and 6 mg/L. Preferably, the aerosol has an inhalable aerosol drug mass density of between 0.35 mg/L and 4 mg/L. More preferably, the aerosol has an inhalable aerosol drug mass density of between 0.5 mg/L and 3.5 mg/L.

Typically, where the aerosol comprises chlorpheniramine, the aerosol has an inhalable aerosol drug mass density of between 0.5 mg/L and 5 mg/L. Preferably, the aerosol has an inhalable aerosol drug mass density of between 0.75 mg/L and 4 mg/L. More preferably, the aerosol has an inhalable aerosol drug mass density of between 1 mg/L and 3 mg/L.

Typically, where the aerosol comprises brompheniramine, carbinoxamine or cyroheptadine, the aerosol has an inhalable aerosol drug mass density of between 0.8 mg/L and 10 mg/L. Preferably, the aerosol has an inhalable aerosol drug mass density of between 1.4 mg/L and 8 mg/L. More preferably, the aerosol has an inhalable aerosol drug mass density of between 2 mg/L and 6 mg/L.

Typically, where the aerosol comprises loratadine, the aerosol has an inhalable aerosol drug mass density of between 2 mg/L and 25 mg/L. Preferably, the aerosol has an inhalable aerosol drug mass density of between 3.5 mg/L and 20 mg/L. More preferably, the aerosol has an inhalable aerosol drug mass density of between 5 mg/L and 15 mg/L.

Typically, where the aerosol comprises promethazine, the aerosol has an inhalable aerosol drug mass density of between 5 mg/L and 60 mg/L. Preferably, the aerosol has an inhalable aerosol drug mass density of between 10 mg/L and 47.5 mg/L. More preferably, the aerosol has an inhalable aerosol drug mass density of between 15 mg/L and 35 mg/L.

Typically, where the aerosol comprises pyrilamine, the aerosol has an inhalable aerosol drug mass density of between 6 mg/L and 70 mg/L. Preferably, the aerosol has an inhalable aerosol drug mass density of between 13 mg/L and 55 mg/L. More preferably, the aerosol has an inhalable aerosol drug mass density of between 20 mg/L and 40 mg/L.

Typically, where the aerosol comprises hydroxyzine, the aerosol has an inhalable aerosol drug mass density of between 2 mg/L and 100 mg/L. Preferably, the aerosol has an inhalable aerosol drug mass density of between 5 mg/L and 75 mg/L. More preferably, the aerosol has an inhalable aerosol drug mass density of between 10 mg/L and 50 mg/L.

Typically, the aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.85. More preferably, the geometric standard deviation is less than 2.7.

Typically, the aerosol is formed by heating a composition containing azatadine, brompheniramine, carbinoxamine, chlorpheniramine, clemastine, cyroheptadine, loratadine, pyrilamine, hydroxyzine, or promethazine to form a vapor and subsequently allowing the vapor to condense into an aerosol.

In a method aspect of the present invention, an antihistamine is delivered to a mammal through an inhalation route. The method comprises: a) heating a composition, wherein the composition comprises at least 5 percent by weight of an antihistamine; and, b) allowing the vapor to cool, thereby forming a condensation aerosol comprising particles, which is inhaled by the mammal. Preferably, the composition that is heated comprises at least 10 percent by weight of an antihistamine. More preferably, the composition comprises 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antihistamine.

Typically, the antihistamine is not one of the following antihistamines: dexmedetomidine, diphenhydramine, doxylamine, loratidine, and promethazine.

In certain embodiments, the composition that is heated comprises at least 15 percent by weight of an antihistamine pharmaceutically acceptable salt. Preferably, the salt is a hydrochloric acid salt, hydrobromic acid salt, acetic acid salt, maleic acid salt, formic acid salt or fumaric acid salt.

Typically, the delivered aerosol particles comprise at least 5 percent by weight of an antihistamine. Preferably, the particles comprise at least 10 percent by weight of an antihistamine. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antihistamine.

Typically, the delivered aerosol has a mass of at least 10 $\mu$g. Preferably, the aerosol has a mass of at least 100 $\mu$g. More preferably, the aerosol has a mass of at least 200 $\mu$g.

Typically, the delivered aerosol particles comprise less than 10 percent by weight of antihistamine degradation products. Preferably, the particles comprise less than 5 percent by weight of antihistamine degradation products. More preferably, the particles comprise less than 2.5, 1, 0.5, 0.1 or 0.03 percent by weight of antihistamine degradation products.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.85. More preferably, the geometric standard deviation is less than 2.7.

Typically, the particles of the delivered condensation aerosol comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the delivered aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered aerosol is formed at a rate greater than 0.25 mg/second. Preferably, the aerosol is formed at a rate greater than 0.5 mg/second. More preferably, the aerosol is formed at a rate greater than 1 or 2 mg/second.

Typically, the delivered condensation aerosol results in a peak plasma concentration of the antihistamine in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h. (arterial measurement).

Typically, the delivered condensation aerosol is used to treat allergy symptoms.

In another method aspect of the present invention, azatadine, brompheniramine, carbinoxamine, chlorpheniramine, clemastine, cyproheptadine, loratadine, pyrilamine, hydroxyzine, or promethazine is delivered to a mammal through an inhalation route. The method comprises: a) heating a composition, wherein the composition comprises at least 5 percent by weight of azatadine, brompheniramine, carbinoxamine, chlorpheniramine, clemastine, cyproheptadine, loratadine, pyrilamine, hydroxyzine, or promethazine; and, b) allowing the vapor to cool, thereby forming a condensation aerosol comprising particles, which is inhaled by the mammal. Preferably, the composition that is heated comprises at least 10 percent by weight of azatadine, brompheniramine, carbinoxamine, chlorpheniramine, clemastine, cyproheptadine, loratadine, pyrilamine, hydroxyzine, or promethazine. More preferably, the composition comprises 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of azatadine, brompheniramine, carbinoxamine, chlorpheniramine, clemastine, cyproheptadine, loratadine, pyrilamine, hydroxyzine, or promethazine.

In certain embodiments, the composition that is heated comprises at least 15 percent by weight of an azatadine, brompheniramine, carbinoxamine, chlorpheniramine, clemastine, cyproheptadine, loratadine, pyrilamine, hydroxyzine, or promethazine pharmaceutically acceptable salt. Preferably, the salt is a hydrochloric acid salt, hydrobromic acid salt, acetic acid salt, maleic acid salt, formic acid salt or fumaric acid salt.

Typically, the delivered aerosol particles comprise at least 5 percent by weight of azatadine, brompheniramine, carbinoxamine, chlorpheniramine, clemastine, cyproheptadine, loratadine, pyrilamine, hydroxyzine, or promethazine. Preferably, the particles comprise at least 10 percent by weight of azatadine, brompheniramine, carbinoxamine, chlorpheniramine, clemastine, cyproheptadine, loratadine, pyrilamine, hydroxyzine, or promethazine. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of azatadine, brompheniramine, carbinoxamine, chlorpheniramine, clemastine, cyproheptadine, loratadine, pyrilamine, hydroxyzine, or promethazine.

Typically, the delivered aerosol has a mass of at least 10 µg. Preferably, the aerosol has a mass of at least 100 µg. More preferably, the aerosol has a mass of at least 200 µg.

Typically, the delivered aerosol particles comprise less than 10 percent by weight of azatadine, brompheniramine, carbinoxamine, chlorpheniramine, clemastine, cyproheptadine, loratadine, pyrilamine, hydroxyzine, or promethazine degradation products. Preferably, the particles comprise less than 5 percent by weight of azatadine, brompheniramine, carbinoxamine, chlorpheniramine, clemastine, cyproheptadine, loratadine, pyrilamine, hydroxyzine, or promethazine degradation products. More preferably, the particles comprise less than 2.5, 1, 0.5, 0.1 or 0.03 percent by weight of azatadine, brompheniramine, carbinoxamine, chlorpheniramine, clemastine, cyproheptadine, loratadine, pyrilamine, hydroxyzine, or promethazine degradation products.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.85. More preferably, the geometric standard deviation is less than 2.7.

Typically, the particles of the delivered condensation aerosol comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the aerosol comprises azatadine, the aerosol has an inhalable aerosol drug mass density of between 0.2 mg/L and 2.5 mg/L. Preferably, the aerosol has an inhalable aerosol drug mass density of between 0.35 mg/L and 2 mg/L. More preferably, the aerosol has an inhalable aerosol drug mass density of between 0.5 mg/L and 1.5 mg/L.

Typically, where the aerosol comprises clemastine, the aerosol has an inhalable aerosol drug mass density of between 0.25 mg/L and 6 mg/L. Preferably, the aerosol has an inhalable aerosol drug mass density of between 0.35 mg/L and 4 mg/L. More preferably, the aerosol has an inhalable aerosol drug mass density of between 0.5 mg/L and 3.5 mg/L.

Typically, where the aerosol comprises chlorpheniramine, the aerosol has an inhalable aerosol drug mass density of between 0.5 mg/L and 5 mg/L. Preferably, the aerosol has an inhalable aerosol drug mass density of between 0.75 mg/L and 4 mg/L. More preferably, the aerosol has an inhalable aerosol drug mass density of between 1 mg/L and 3 mg/L.

Typically, where the aerosol comprises brompheniramine, carbinoxamine or cyproheptadine, the aerosol has an inhalable aerosol drug mass density of between 0.8 mg/L and 10 mg/L. Preferably, the aerosol has an inhalable aerosol drug mass density of between 1.4 mg/L and 8 mg/L. More preferably, the aerosol has an inhalable aerosol drug mass density of between 2 mg/L and 6 mg/L.

Typically, where the aerosol comprises loratadine, the aerosol has an inhalable aerosol drug mass density of between 2 mg/L and 25 mg/L. Preferably, the aerosol has an inhalable aerosol drug mass density of between 3.5 mg/L and 20 mg/L. More preferably, the aerosol has an inhalable aerosol drug mass density of between 5 mg/L and 15 mg/L.

Typically, where the aerosol comprises promethazine, the aerosol has an inhalable aerosol drug mass density of between 5 mg/L and 60 mg/L. Preferably, the aerosol has an inhalable aerosol drug mass density of between 10 mg/L and 47.5 mg/L. More preferably, the aerosol has an inhalable aerosol drug mass density of between 15 mg/L and 35 mg/L.

Typically, where the aerosol comprises hydroxyzine, the aerosol has an inhalable aerosol drug mass density of between 2 mg/L and 100 mg/L. Preferably, the aerosol has an inhalable aerosol drug mass density of between 5 mg/L and 75 mg/L. More preferably, the aerosol has an inhalable aerosol drug mass density of between 10 mg/L and 50 mg/L.

Typically, where the aerosol comprises pyrilamine, the aerosol has an inhalable aerosol drug mass density of between 6 mg/L and 70 mg/L. Preferably, the aerosol has an inhalable aerosol drug mass density of between 13 mg/L and 55 mg/L. More preferably, the aerosol has an inhalable aerosol drug mass density of between 20 mg/L and 40 mg/L.

Typically, the delivered aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered aerosol is formed at a rate greater than 0.25 mg/second. Preferably, the aerosol is formed at a rate greater than 0.5 mg/second. More preferably, the aerosol is formed at a rate greater than 1 or 2 mg/second.

Typically, where the aerosol comprises azatadine, between 0.2 mg and 2.5 mg of azatadine is delivered to the mammal in a single inspiration. Preferably, between 0.35 mg and 2 mg of azatadine is delivered to the mammal in a single inspiration. More preferably, between 0.5 mg and 1.5 mg of azatadine is delivered to the mammal in a single inspiration.

Typically, where the aerosol comprises clemastine, between 0.25 mg and 6 mg of clemastine is delivered to the mammal in a single inspiration. Preferably, between 0.35 mg and 4 mg of clemastine is delivered to the mammal in a single inspiration. More preferably, between 0.5 mg and 3.5 mg of clemastine is delivered to the mammal in a single inspiration.

Typically, where the aerosol comprises chlorpheniramine, between 0.5 mg and 5 mg of chlorpheniramine is delivered to the mammal in a single inspiration. Preferably, between 0.75 mg and 4 mg of chlorpheniramine is delivered to the mammal in a single inspiration. More preferably, between 1 mg and 3 mg of chlorpheniramine is delivered to the mammal in a single inspiration.

Typically, where the aerosol comprises brompheniramine, carbinoxamine or cyproheptadine, between 0.8 mg and 10 mg of brompheniramine, carbinoxamine or cyproheptadine is delivered to the mammal in a single inhalation. Preferably, between 1.4 mg and 8 mg of brompheniramine, carbinoxamine or cyproheptadine is delivered to the mammal in a single inhalation. More preferably, between 2 mg and 6 mg of brompheniramine, carbinoxamine or cyproheptadine is delivered to the mammal in a single inhalation.

Typically, where the aerosol comprises loratadine, between 2 mg and 25 mg or loratadine is delivered to the mammal in a single inhalation. Preferably, between 3.5 mg and 20 mg of loratadine is delivered to the mammal in a single inspiration. More preferably, between 5 mg and 15 mg of loratadine is delivered to the mammal in a single inspiration.

Typically, where the aerosol comprises promethazine, between 5 mg and 60 mg of promethazine is delivered to the mammal in a single inspiration. Preferably, between 10 mg and 47.5 mg of promethazine is delivered to the mammal in a single inspiration. More preferably, between 15 mg and 35 mg of promethazine is delivered to the mammal in a single inspiration.

Typically, where the aerosol comprises hydroxyzine, between 2 mg and 100 mg of hydroxyzine is delivered to the mammal in a single inspiration. Preferably, between 5 mg and 75 mg of hydroxyzine is delivered to the mammal in a single inspiration. More preferably, between 10 mg and 50 mg of hydroxyzine is delivered to the mammal in a single inspiration.

Typically, where the aerosol comprises pyrilamine, between 6 mg and 70 mg of pyrilamine is delivered to the mammal in a single inspiration. Preferably, between 13 mg and 55 mg of pyrilamine is delivered to the mammal in a single inspiration. More preferably, between 20 mg and 40 mg of pyrilamine is delivered to the mammal in a single inspiration.

Typically, the delivered condensation aerosol results in a peak plasma concentration of azatadine, brompheniramine, carbinoxamine, chlorpheniramine, clemastine, cyproheptadine, loratadine, pyrilamine, hydroxyzine, or promethazine in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h. (arterial measurement).

Typically, the delivered condensation aerosol is used to treat allergy symptoms.

In a kit aspect of the present invention, a kit for delivering an antihistamine through an inhalation route to a mammal is provided which comprises: a) a composition comprising at least 5 percent by weight of an antihistamine; and, b) a device that forms an antihistamine containing aerosol from the composition, for inhalation by the mammal. Preferably, the composition comprises at least 10 percent by weight of an antihistamine. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antihistamine.

Typically, the device contained in the kit comprises: a) an element for heating the antihistamine composition to form a vapor; b) an element allowing the vapor to cool to form an aerosol; and, c) an element permitting the mammal to inhale the aerosol.

In another kit aspect of the present invention, a kit for delivering azatadine, brompheniramine, carbinoxamine, chlorpheniramine, clemastine, cyproheptadine, loratadine, pyrilamine, hydroxyzine, or promethazine an inhalation route to a mammal is provided which comprises: a) a composition comprising at least 5 percent by weight of azatadine, brompheniramine, carbinoxamine, chlorpheniramine, clemastine, cyproheptadine, loratadine, pyrilamine, hydroxyzine, or promethazine; and, b) a device that forms a azatadine, brompheniramine, carbinoxamine, chlorpheniramine, clemastine, cyproheptadine, loratadine, pyrilamine, hydroxyzine, or promethazine containing aerosol from the composition, for inhalation by the mammal. Preferably, the composition comprises at least 10 percent by weight of azatadine, brompheniramine, carbinoxamine, chlorpheniramine, clemastine, cyproheptadine, loratadine, pyrilamine, hydroxyzine, or promethazine. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of azatadine, brompheniramine, carbinoxamine, chlorpheniramine, clemastine, cyproheptadine, loratadine, pyrilamine, hydroxyzine, or promethazine.

Typically, the device contained in the kit comprises: a) an element for heating the azatadine, brompheniramine, carbinoxamine, chlorpheniramine, clemastine, cyproheptadine, loratadine, pyrilamine, hydroxyzine, or promethazine composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
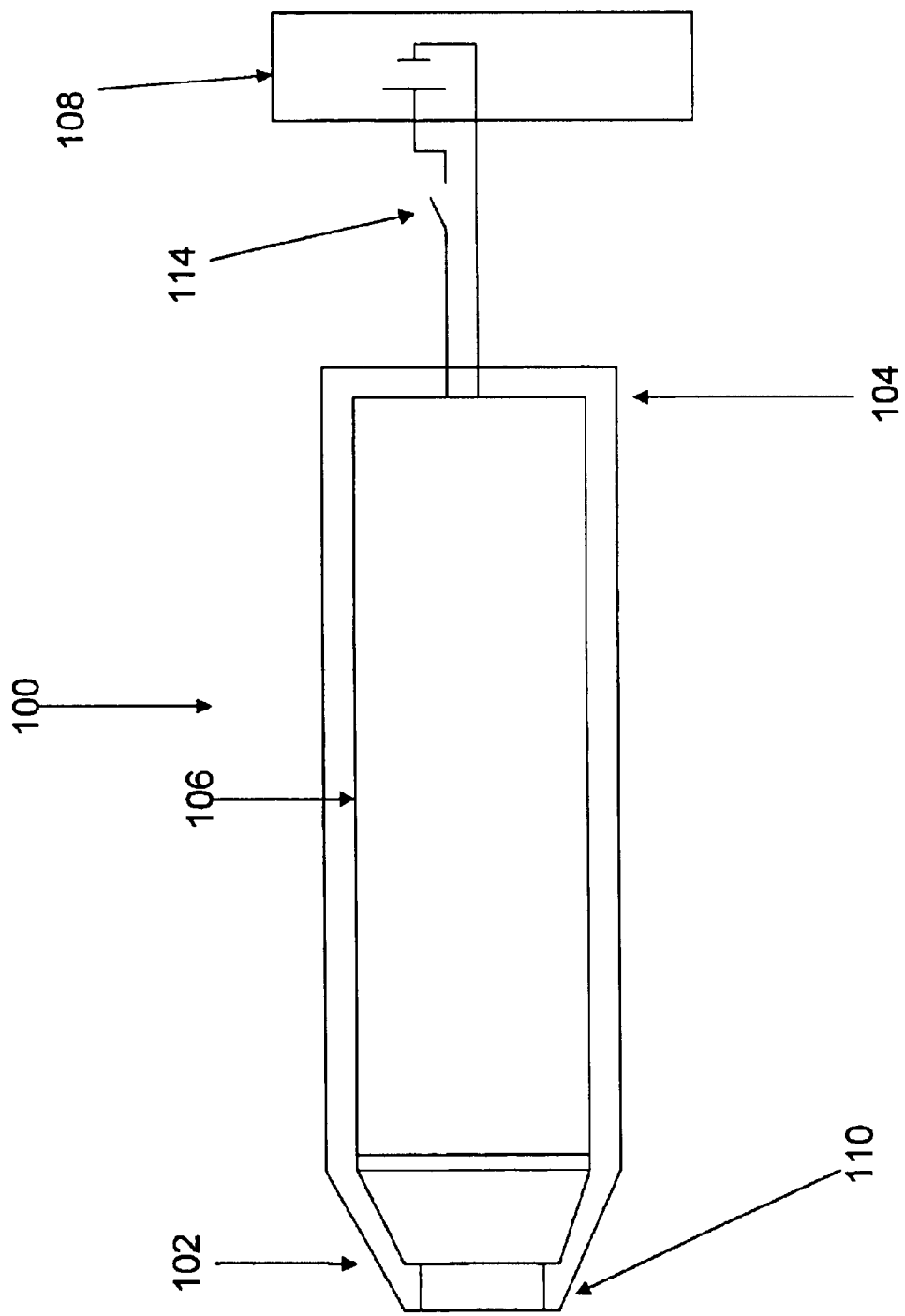
FIG. 1 shows a device used to deliver antihistamine containing aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of antihistamine per unit volume of aerosol.

"Aerosol mass density" refers to the mass of particulate matter per unit volume of aerosol.

"Aerosol particle density" refers to the number of particles per unit volume of aerosol.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Antihistamine degradation product" refers to a compound resulting from a chemical modification of an antihistamine. The modification, for example, can be the result of a thermally or photochemically induced reaction. Such reactions include, without limitation, oxidation and hydrolysis.

"Azatadine" refers to 6,11-dihydro-11-(1-methyl-4-piperidinylidene)-5H-benzo[5,6]cyclohepta[1,2-b]pyridine.

"Azatadine degradation product" refers to a compound resulting from a chemical modification of azatadine. The modification, for example, can be the result of a thermally or photochemically induced reaction. Such reactions include, without limitation, oxidation and hydrolysis.

"Brompheniramine" refers to 1-(p-bromophenyl)-1-(2-pyridyl)-3-N,N-dimethylaminopropane.

"Brompheniramine degradation product" refers to a compound resulting from a chemical modification of brompheniramine. The modification, for example, can be the result of a thermally or photochemically induced reaction. Such reactions include, without limitation, oxidation and hydrolysis.

"Carbinoxamine" refers to 2-[p-chloro-α-(2-dimethylaminoethoxy)benzyl]-pyridine.

"Carbinoxamine degradation product" refers to a compound resulting from a chemical modification of carbinoxamine. The modification, for example, can be the result of a thermally or photochemically induced reaction. Such reactions include, without limitation, oxidation and hydrolysis.

"Chlorpheniramine" refers to 1-(p-chlorophenyl)-1-(2-pyridyl)-3-N,N-dimethylaminopropane.

"Chlorpheniramine degradation product" refers to a compound resulting from a chemical modification of chlorpheniramine. The modification, for example, can be the result of a thermally or photochemically induced reaction. Such reactions include, without limitation, oxidation and hydrolysis. An example of a degradation product is a compound of molecular formula $C_{12}H_8NOCL$.

"Clemastine" refers to 2-[2-[1-(4-chlorophenyl)-1-phenyl-ethoxy]ethyl]-1-methylpyrrolidine.

"Clemastine degradation product" refers to a compound resulting from a chemical modification of clemastine. The modification, for example, can be the result of a thermally or photochemically induced reaction. Such reactions include, without limitation, oxidation and hydrolysis. An example of a degradation product is $C_{14}H_{13}OCl$ (removal of sidechain from oxygen, yielding an alcohol).

"Condensation aerosol" refers to an aerosol formed by vaporization of a substance followed by condensation of the substance into an aerosol.

"Cyproheptadine" refers to 4-(5H-dibenzo[a,d]cyclohepten-5-ylidene)-1-methylpiperidine.

"Cyproheptadine degradation product" refers to a compound resulting from a chemical modification of cyproheptadine. The modification, for example, can be the result of a thermally or photochemically induced reaction. Such reactions include, without limitation, oxidation and hydrolysis. An example of a degradation product is the N-oxide of cyproheptadine ($C_{21}H_{21}NO$).

"Hydroxyzine" refers to 2-[2-[4-[(4-chlorophenyl)phenylmethyl]-1-piperazinyl]-ethoxy]ethanol.

"Hydroxyzine degradation product" refers to a compound resulting from a chemical modification of hydroxyzine. The modification, for example, can be the result of a thermally or photochemically induced reaction. Such reactions include, without limitation, oxidation and hydrolysis. An example of a degradation product is a compound of molecular formula $C_{13}H_9OCl$ (a chloro benzophenone).

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Loratadine" refers to ethyl 4-(8-chloro-5,6-dihydro-11H-benzo[5,6]cyclohepta[1,2-b]pyridine-11-ylidene)-1-piperidinecarboxylate "Loratadine degradation product" refers to a compound resulting from a chemical modification of loratadine. The modification, for example, can be the result of a thermally or photochemically induced reaction. Such reactions include, without limitation, oxidation and hydrolysis.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Promethazine" refers to 10-(2-dimethylaminopropyl) phenothiazine.

"Promethazine degradation product" refers to a compound resulting from a chemical modification of promethazine. The modification, for example, can be the result of a thermally or photochemically induced reaction. Such reactions include, without limitation, oxidation and hydrolysis. An example of a degradation product is a compound of molecular formula $C_{12}H_9NOS$ (a sulfoxide).

"Pyrilamine" refers to N-[(4-methoxyphenyl)methyl]-N', N'-dimethyl-N-2-pyridinyl-1,2-ethanediamine.

"Pyrilamine degradation product" refers to a compound resulting from a chemical modification of pyrilamine. The modification, for example, can be the result of a thermally or photochemically induced reaction. Such reactions include, without limitation, oxidation and hydrolysis. An example of a degradation product is 4-methoxy-benzaldehyde.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized antihistamine produced by an inhalation device per unit time.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Antihistamine Containing Aerosols

Any suitable method is used to form the aerosols of the present invention. A preferred method, however, involves heating a composition comprising an antihistamine to form a vapor, followed by cooling of the vapor such that it condenses to provide an antihistamine comprising aerosol (condensation aerosol). The composition is heated in one of four forms: as pure active compound (e.g., pure azatadine, brompheniramine, carbinoxamine, chlorpheniramine, clemastine, cyproheptadine, loratadine, pyrilamine, hydroxyzine, or promethazine); as a mixture of active compound and a pharmaceutically acceptable excipient; as a salt form of the pure active compound; and, as a mixture of active compound salt form and a pharmaceutically acceptable excipient.

Salt forms of antihistamines (e.g., azatadine, brompheniramine, carbinoxamine, chlorpheniramine, clemastine, cyproheptadine, loratadine, pyrilamine, hydroxyzine, or promethazine) are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with the antihistamine. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2$/g from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the antihistamine compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Antihistamine Containing Aerosols

Antihistamine containing aerosols of the present invention are delivered to a mammal using an inhalation device. Where the aerosol is a condensation aerosol, the device has at least three elements: an element for heating an antihistamine containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver an antihistamine containing aerosol is described in reference to FIG. 1. Delivery device 100 has a proximal end 102 and a distal end 104, a heating module 106, a power source 108, and a mouthpiece 110. An antihistamine composition is deposited on a surface 112 of heating module 106. Upon activation of a user activated switch 114, power source 108 initiates heating of heating module 106 (e.g, through ignition of combustible fuel or passage of current through a resistive heating element). The antihistamine composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of antihistamine containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Antihistamine Containing Aerosols

The dosage amount of antihistamine in aerosol form is generally no greater than twice the standard dose of the drug given orally. For instance, for the treatment of allergy symptoms azatadine, brompheniramine, carbinoxamine, chlorpheniramine, clemastine, cyproheptadine, loratadine, pyrilamine, hydroxyzine and promethazine are typically provided orally at the following respective strengths: 1 mg, 4 mg, 4 mg, 2 mg, 1.34 mg, 4 mg, 10 mg, 30 mg, 25 mg, and 25 mg. As aerosols, the compounds are generally provided in the following amounts per inspiration for the same indication: azatadine, 0.2 mg to 2.5 mg; clemastine, 0.25 mg to 6 mg; chlorpheniramine, 0.5 mg to 5 mg; brompheniramine, 0.8 mg to 10 mg; carbinoxamine, 0.8 mg to 10 mg; cyproheptadine, 0.8 mg to 10 mg; loratadine, 2 mg to 25 mg; promethazine, 5 mg to 60 mg; hydroxyzine, 2 mg to 100 mg; and, pyrilamine, 6 mg to 70 mg. A typical dosage of an antihistamine aerosol is either administered as a single inhalation or as a series of inhalations taken within an hour or less (dosage equals sum of inhaled amounts). Where the drug is administered as a series of inhalations, a different amount may be delivered in each inhalation.

One can determine the appropriate dose of an antihistamine containing aerosol to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Antihistamine Containing Aerosols

Purity of an antihistamine containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of antihistamine degradation products.

Particle size distribution of an antihistamine containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi*D^3*\phi/6$, where D is a typical particle diameter in the size range (generally, the mean boundary MMADs defining the size range) in microns, $\phi$, is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering an antihistamine containing aerosol into a confined chamber via an inhalation device over a set period of time (e.g., 3 s). Where the aerosol is pure antihistamine, the amount of drug collected in the chamber is measured as described above. The rate of drug aerosol formation is equal to the amount of antihistamine collected in the chamber divided by the duration of the collection time. Where the antihistamine containing aerosol comprises a pharmaceutically acceptable excipient, multiplying the rate of aerosol formation by the percentage of antihistamine in the aerosol provides the rate of drug aerosol formation.

Utility of Antihistamine Containing Aerosols

Antihistamine containing aerosols are typically used for the treatment of allergy symptoms.

The following examples are meant to illustrate, rather than limit, the present invention.

Hydroxyzine dihydrochloride, brompheniramine maleate, carbinoxamine maleate, clemastine fumarate, cyproheptadine hydrochloride, pyrilamine maleate, and promethazine hydrochloride are commercially available from Sigma (www.sigma-aldrich.com). Antihistamines can also be isolated from compositions such as RYNATAN®, DIMETANE®, RONDEC®, SINUTAB®, TAVIST®, PERIACTIN®, CLARITIN®, RYNA-12™, and PHENERGAN® using standard methods in the art.

EXAMPLE 1

General Procedure for Obtaining Free Base of an Antihistamine Salt

Approximately 1 g of salt (e.g., mono hydrochloride) is dissolved in deionized water (~30 mL). Three equivalents of sodium hydroxide (1 N $NaOH_{aq}$) is added dropwise to the solution, and the pH is checked to ensure it is basic. The aqueous solution is extracted four times with dichloromethane (~50 mL), and the extracts are combined, dried ($Na_2SO_4$) and filtered. The filtered organic solution is concentrated using a rotary evaporator to provide the desired free base. If necessary, purification of the free base is performed using standard methods such as chromatography or recrystallization.

EXAMPLE 2

General Procedure for Volatilizing Compounds

A solution of drug in approximately 120 μL dichloromethane is coated on a 3 cm×8 cm piece of aluminum foil. The dichloromethane is allowed to evaporate. The coated foil is wrapped around a 300 watt halogen tube (Feit Electric Company, Pico Rivera, Calif.), which is inserted into a glass tube sealed at one end with a rubber stopper. Running 60 V of alternating current (driven by line power controlled by a variac) through the bulb for 5–11 s affords thermal vapor (including aerosol), which is collected on the glass tube walls. Reverse-phase HPLC analysis with detection by absorption of 225 nm light is used to determine the purity of the aerosol. (When desired, the system is flushed through with argon prior to volatilization.)

Table 1, which follows, provides data from drugs volatilized using the above-recited general procedure. Current is typically run for 5 s after an aerosol is first noticed. To obtain higher purity aerosols, one can coat a lesser amount of drug, yielding a thinner film to heat. A linear decrease in film thickness is associated with a linear decrease in impurities.

TABLE 1

| Compound | Aerosol Purity | Argon Used |
|---|---|---|
| Azatadine | 99.6% | No |
| Brompheniramine | 99.0% | No |
| Brompheniramine | 99.3% | Yes |
| Brompheniramine Maleate | 99.6% | No |
| Brompheniramine Maleate | 100% | Yes |
| Carbinoxamine | 94.8% | Yes |
| Carbinoxamine Maleate | 99.0% | No |
| Carbinoxamine Maleate | 100% | Yes |
| Chlorpheniramine | 98.4% | No |
| Chlorpheniramine Maleate | 99.6% | No |
| Chlorpheniramine | 100% | Yes |
| Clemastine | 94.3% | No |
| Cyproheptadine | 100% | No |

TABLE 1-continued

| Compound | Aerosol Purity | Argon Used |
|---|---|---|
| Cyroheptadine | 99.6% | No |
| Hydroxyzine | 98.6% | No |
| Loratadine | 99.0% | No |
| Loratadine | 99.6% | Yes |
| Pyrilamine | 98.8% | No |
| Pyrilamine | 99.5% | Yes |
| Promethazine | 94.5% | Yes |

EXAMPLE 3

Particle Size, Particle Density, and Rate of Inhalable Particle Formation of Loratadine Aerosol A solution of 12.1 mg loratadine in 200 μL dichloromethane was spread out in a thin layer on the central portion of a 3.5 cm×7 cm sheet of aluminum foil. The dichloromethane was allowed to evaporate. Assuming a drug density of about 1g/cc, the calculated thickness of the loratadine thin layer on the 24.5 cm² aluminum solid support, after solvent evaporation, is about 4.9 microns. The aluminum foil was wrapped around a 300 watt halogen tube, which was inserted into a T-shaped glass tube. Both of the openings of the tube were left open and the third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 1.1 microns with a geometric standard deviation of 2.6. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm³). The inhalable aerosol particle density is the sum of the numbers of particles collected on impactor stages 3 to 8 divided by the collection volume of 1 L, giving an inhalable aerosol particle density of $5.2 \times 10^7$ particles/mL. The rate of inhalable aerosol particle formation is the sum of the numbers of particles collected on impactor stages 3 through 8 divided by the formation time of 6 s, giving a rate of inhalable aerosol particle formation of $8.7 \times 10^9$ particles/second.

Table 1: Determination of the characteristics of a loratadine condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.0 | 0 |
| 1 | 5.8–9.0 | 7.4 | 0.1 | $4.7 \times 10^5$ |
| 2 | 4.7–5.8 | 5.25 | 0.0 | 0 |
| 3 | 3.3–4.7 | 4.0 | 0.1 | $3.0 \times 10^6$ |
| 4 | 2.1–3.3 | 2.7 | 0.6 | $5.8 \times 10^7$ |
| 5 | 1.1–2.1 | 1.6 | 0.0 | 0 |
| 6 | 0.7–1.1 | 0.9 | 0.4 | $1.1 \times 10^9$ |
| 7 | 0.4–0.7 | 0.55 | 0.3 | $3.4 \times 10^9$ |
| 8 | 0–0.4 | 0.2 | 0.2 | $4.8 \times 10^{10}$ |

EXAMPLE 4

Drug Mass Density and Rate of Drug Aerosol Formation of Loratadine Aerosol

A solution of 10.4 mg loratadine in 200 μL dichloromethane was spread out in a thin layer on the central portion of a 3.5 cm×7 cm sheet of aluminum foil. The dichloromethane was allowed to evaporate. Assuming a drug density of about 1g/cc, the calculated thickness of the loratadine thin layer on the 24.5 cm² aluminum solid support, after solvent evaporation, is about 4.2 microns. The aluminum foil was wrapped around a 300 watt halogen tube, which was inserted into a T-shaped glass tube. Both of the openings of the tube were left open and the third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 flask for approximately 30 minutes. The flask was then extracted with acetonitrile and the extract analyzed by HPLC with detection by light absorption at 225 nm. Comparison with standards containing known amounts of loratadine revealed that 1.0 mg of >99% pure loratadine had been collected in the flask, resulting in an aerosol drug mass density of 1.0 mg/L. The aluminum foil upon which the loratadine had previously been coated was weighed following the experiment. Of the 10.4 mg originally coated on the aluminum, 3.8 mg of the material was found to have aerosolized in the 6 s time period, implying a rate of drug aerosol formation of 0.6 mg/s.

What is claimed is:

1. A composition for delivery of an antihistamine comprising a condensation aerosol
    a) formed by volatilizing an antihistamine under conditions effective to produce a heated vapor of the antihistamine and condensing the heated vapor of the antihistamine to form condensation aerosol particles,
    b) wherein said condensation aerosol particles are characterized by less than 5% antihistamine degradation products, and
    c) wherein the aerosol MMAD is less than 3 microns.

2. The composition according to claim 1, wherein the antihistamine is selected from the group consisting of azatadine, brompheniramine, carbinoxamine, chlorpheniramine, clemastine, cyroheptadine, loratadine, pyrilamine, hydroxyzine, or promethazine.

3. The composition according to claim 2, wherein the condensation aerosol particles comprise less than 2.5 percent by weight of azatadine, brompheniramine, carbinoxamine, chlorpheniramine, clemastine, cyproheptadine, loratadine, pyrilamine, hydroxyzine, or promethazine degradation products.

4. The composition according to claim 2, wherein the condensation aerosol particles comprise at least 90 percent by weight of azatadine, brompheniramine, carbinoxamine, chlorpheniramine, clemastine, cyproheptadine, loratadine, pyrilamine, hydroxyzine, or promethazine.

5. The composition according to claim 4, wherein the condensation aerosol has a mass median aerodynamic diameter less than 2 microns.

6. The composition according to claim 5, wherein the condensation aerosol particles comprise at least 97 percent by weight of azatadine, brompheniramine, chlorpheniramine, cyproheptadine, loratadine, hydroxyzine, or pyrilamine.

7. A method of producing an antihistamine in an aerosol form comprising:
   a) volatilizing an antihistamine under conditions effective to produce a heated vapor of the antihistamine, and
   b) during said volatilizing, passing air through the heated vapor to produce aerosol particles of the antihistamine comprising less than 5% drug degradation products and an aerosol having an MMAD less than 3 μm.

8. The method according to claim 7, wherein the antihistamine is selected from the group consisting of azatadine, brompheniramine, carbinoxamine, chlorpheniramine, clemastine, cyproheptadine, loratadine, pyrilamine, hydroxyzine, or promethazine.

9. The method according to claim 7, wherein said volatilizing includes heating a thin layer which includes the antihistamine and which is on a solid support having the surface texture of a metal foil, to a temperature sufficient to volatilize the antihistamine from the thin layer.

10. The method according to claim 8, wherein the aerosol particles comprise less than 2.5 percent by weight of azatadine, brompheniramine, carbinoxamine, chlorpheniramine, clemastine, cyproheptadine, loratadine, pyrilamine, hydroxyzine, or promethazine degradation products.

11. The method according to claim 8, wherein the aerosol particles comprise at least 90 percent by weigh of azatadine, brompheniramine, carbinoxamine, chlorpheniramine, clemastine, cyproheptadine, loratadine, pyrilamine, hydroxyzine, or promethazine.

12. The method according to claim 11, wherein the aerosol has a mass median aerodynamic diameter less than 2 microns.

13. The method according to claim 12, wherein the aerosol particles comprise at least 97 percent by weight of azatadine, brompheniramine, carbinoxamine, chlorpheniramine, clemastine, cyproheptadine, loratadine, pyrilamine, hydroxyzine, or promethazine.

14. The method according to claim 10, wherein the thin layer which includes azatadine, brompheniramine, carbinoxamine, chlorpheniramine, clemastine, cyproheptadine, loratadine, pyrilamine, hydroxyzine, or promethazine on said solid support surface has a thickness between 4.2 and 4.9 microns.

15. The method according to claim 7, wherein the aerosol particles are formed at a rate of greater than 0.5 mg/sec.

16. The method according to claim 7, wherein the antihistamine is in a free base form.

* * * * *